United States Patent
Averett et al.

(10) Patent No.: US 9,833,003 B2
(45) Date of Patent: *Dec. 5, 2017

(54) TITANIUM DIOXIDE PHOTOCATALYTIC COMPOSITIONS AND USES THEREOF

(71) Applicant: WELL Shield LLC, Boca Raton, FL (US)

(72) Inventors: Stewart Benson Averett, Lighthouse Point, FL (US); Devron R. Averett, Berkeley, CA (US)

(73) Assignee: WELL Shield LLC, Boca Raton, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/197,867

(22) Filed: Jun. 30, 2016

(65) Prior Publication Data

US 2016/0302422 A1    Oct. 20, 2016

Related U.S. Application Data

(60) Continuation of application No. 14/713,020, filed on May 15, 2015, now Pat. No. 9,392,795, which is a
(Continued)

(51) Int. Cl.
*A01N 59/16* (2006.01)
*A01N 59/20* (2006.01)
(Continued)

(52) U.S. Cl.
CPC ............. *A01N 59/16* (2013.01); *A01N 59/00* (2013.01); *A01N 59/20* (2013.01); *B01J 21/063* (2013.01);
(Continued)

(58) Field of Classification Search
CPC ........ A01N 59/00; A01N 59/16; A01N 59/20; B01J 21/063; B01J 23/04; B01J 23/06;
(Continued)

(56) References Cited

U.S. PATENT DOCUMENTS

| | | |
|---|---|---|
| 4,882,166 A | 11/1989 | Graham et al. |
| 6,387,844 B1 | 5/2002 | Fujishima et al. |

(Continued)

FOREIGN PATENT DOCUMENTS

| | | |
|---|---|---|
| CN | 101607736 A | 12/2009 |
| CN | 101905166 | 12/2010 |

(Continued)

OTHER PUBLICATIONS

Zou et al., "Zn- and La-modified TiO2 photocatalysts for the isomerization of norbornadiene to quadricyclane," Journal of Molecular Catalysis A: Chemical, vol. 286, Issues 1-2, pp. 63-69 (2008).

(Continued)

*Primary Examiner* — Aradhana Sasan
(74) *Attorney, Agent, or Firm* — Mintz, Levin, Cohn, Ferris, Glovsky and Popeo, P.C.

(57) ABSTRACT

Provided is a photocatalytic composition comprising zinc (Zn) doped titanium dioxide ($TiO_2$) nanoparticles, wherein the ratio of titanium dioxide nanoparticles to zinc is from about 5 to about 150. The photocatalytic composition absorbs electromagnetic radiation in a wavelength range from about 200 nm to about 500 nm, and the absorbance of light of wavelengths longer than about 450 nm is less than 50% the absorbance of light of wavelengths shorter than about 350 nm.

20 Claims, 5 Drawing Sheets

Related U.S. Application Data continuation of application No. 14/069,682, filed on Nov. 1, 2013, now Pat. No. 9,055,751, which is a division of application No. 13/463,495, filed on May 3, 2012, now Pat. No. 8,609,121.

(60) Provisional application No. 61/482,393, filed on May 4, 2011.

(51) Int. Cl.

| | |
|---|---|
| *A01N 59/00* | (2006.01) |
| *B01J 35/02* | (2006.01) |
| *B01J 35/00* | (2006.01) |
| *B01J 21/06* | (2006.01) |
| *B01J 37/03* | (2006.01) |
| *B01J 23/06* | (2006.01) |
| *B01J 23/46* | (2006.01) |
| *B01J 23/42* | (2006.01) |
| *B01J 23/36* | (2006.01) |
| *B01J 23/38* | (2006.01) |
| B01J 23/04 | (2006.01) |
| B01J 23/14 | (2006.01) |
| B01J 23/28 | (2006.01) |
| B01J 23/50 | (2006.01) |
| B01J 23/745 | (2006.01) |
| B82Y 5/00 | (2011.01) |
| B82Y 30/00 | (2011.01) |

(52) U.S. Cl.
CPC ............ *B01J 23/06* (2013.01); *B01J 35/004* (2013.01); *B01J 35/006* (2013.01); *B01J 35/0013* (2013.01); *B01J 35/023* (2013.01); *B01J 37/036* (2013.01); B01J 23/04 (2013.01); B01J 23/14 (2013.01); B01J 23/28 (2013.01); B01J 23/36 (2013.01); B01J 23/42 (2013.01); B01J 23/462 (2013.01); B01J 23/464 (2013.01); B01J 23/466 (2013.01); B01J 23/50 (2013.01); B01J 23/745 (2013.01); B82Y 5/00 (2013.01); B82Y 30/00 (2013.01); Y10S 977/773 (2013.01); Y10S 977/811 (2013.01); Y10S 977/906 (2013.01)

(58) Field of Classification Search
CPC ... B01J 23/14; B01J 23/28; B01J 23/36; B01J 23/42; B01J 23/462; B01J 23/464; B01J 23/466; B01J 23/50; B01J 23/745; B01J 35/006; B01J 35/023; B01J 37/036; B82Y 30/00; B82Y 5/00; Y10S 977/773; Y10S 977/811; Y10S 977/906
See application file for complete search history.

(56) References Cited

U.S. PATENT DOCUMENTS

| | | | |
|---|---|---|---|
| 6,589,912 | B2 | 7/2003 | Kawai |
| 6,878,191 | B2 | 4/2005 | Escaffre et al. |
| 8,609,121 | B2 | 12/2013 | Averett et al. |
| 9,055,751 | B2 | 6/2015 | Averett et al. |
| 9,144,242 | B2 | 9/2015 | Averett et al. |
| 2002/0096121 | A1 | 7/2002 | Ingman et al. |
| 2002/0187082 | A1 | 12/2002 | Wu et al. |
| 2003/0209501 | A1 | 11/2003 | Leung |
| 2004/0060677 | A1 | 4/2004 | Huang |
| 2005/0191505 | A1 | 9/2005 | Akarsu et al. |
| 2005/0214533 | A1 | 9/2005 | Shimosaki et al. |
| 2006/0246149 | A1 | 11/2006 | Buchholz et al. |
| 2008/0031832 | A1 | 2/2008 | Wakefield et al. |
| 2009/0068089 | A1 | 3/2009 | Hussain et al. |
| 2009/0104086 | A1 | 4/2009 | Zax et al. |
| 2009/0169425 | A1 | 7/2009 | Park et al. |
| 2009/0241496 | A1 | 10/2009 | Pintault et al. |
| 2010/0021710 | A1 | 1/2010 | Hunt et al. |
| 2010/0119461 | A1 | 5/2010 | Bicard-Benhamou et al. |
| 2010/0197495 | A1 | 8/2010 | Filippini et al. |
| 2012/0010314 | A1* | 1/2012 | Charpentier ....... C08G 18/0823 521/157 |

FOREIGN PATENT DOCUMENTS

| | | |
|---|---|---|
| CN | 102139206 A | 8/2011 |
| JP | 2001-286226 | 10/2001 |
| JP | 2001-314882 | 11/2001 |
| JP | 2003-340289 A * | 12/2003 ............. B01J 35/02 |
| JP | 2005-040769 | 2/2005 |
| JP | 2006-321721 | 11/2006 |
| JP | 2009-084542 A | 4/2009 |
| KR | 2000009824 A | 2/2000 |
| KR | 20010048235 | 6/2001 |
| KR | 2005000389 | 1/2005 |
| WO | 2004/037301 | 5/2004 |
| WO | 2007/026387 | 3/2007 |
| WO | 2008/043396 A1 | 4/2008 |
| WO | 2008/135093 A1 | 11/2008 |
| WO | 2009/030641 A1 | 3/2009 |
| WO | 2010/115720 A2 | 10/2010 |
| WO | 2011/033377 A2 | 3/2011 |

OTHER PUBLICATIONS

Zhao et al., "Zn-doped $TiO_2$ nanoparticles with high photocatalytic activity synthesized by hydrogen-oxygen diffusion flame," Applied Catalysis B: Environmental, vol. 79, Issue 3, pp. 208-215 (2008).
Srinivasan et al., "Synergistic effects of sulfation and co-doping on the visible light photocatalysis of $TiO_2$," Journal of Alloys and Compounds, vol. 424, Issues 1-2, pp. 322-326 (2006).
Mar. 2, 2016 Office Action issued in Japanese Application No. 2014-509443 (with Partial English Translation).
U.S. Appl. No. 14/713,020, filed May 15, 2015.
Yao et al., "Photocatalytic disinfection of phytopathogenic bacteria by dye-sensitized $TiO_2$ thin film activated visible light," Surface and Coatings Technology (2007), 202(4-7), 1329-1332.
Cui et al., "Application of anatase $TiO_2$ sol derived from peroxotitannic acid in crop diseases control and regulation," Nanotech Conference & Expo 2009: An Interdisciplinary Forum on Nanotechnology Biotechnology and Microtechnology, Houston, TX, United States, May 3-7, 2009 (2009), vol. 2, 286-289.
Zhang et al., "Photobiological effects of nano-$TiO_2$ semiconductors sol," Wuji Cailiao Xuebao (2008), 23(1), 55-60.
Yao et al., "Photocatalytic effects of Tio2/Fe thin film with visible light on cellular surface ulstrastructure and genomic DNA of bacteria," Surface and Coatings Technology (2007), 201(15), 6882-6885.
Kim et al., "Disinfection of Iceberg Lettuce by Titanium Dioxide-UV Photocatalytic Reaction," Journal of Food Protection, (Sep. 2009) vol. 72, No. 9, pp. 1916-1922.
Zhang et al., "Effects of nano—$TiO_2$ semiconductor sol on prevention from plant diseases," Nanoscience, (May 2007) vol. 12, No. 1, pp. 1-6.
International Search Report and Written Opinion, International Application No. PCT/US12/36337, dated Sep. 28, 2012.
Fujishima et al, "Electrochemical photolysis of water at a semiconductor electrode," Nature, vol. 238, pp. 37-38, 1972.
Chen et al., "Titanium Dioxide Nanomaterials: Synthesis, Properties, Modifications, and Applications," Chemical Reviews, vol. 107, pp. 2891-2959, 2007.
Matsunaga et al., "Photoelectrochemical sterilization of microbial cells by semiconductor powders," FEMS Microbiology Letters, vol. 29, pp. 211-214, 1985.
Tsuang et al., "Studies of photokilling of bacteria using titanium dioxide nanoparticles," Artificial Organs, vol. 32, pp. 167-174, 2008.

(56) References Cited

OTHER PUBLICATIONS

Choi et al., "Photocatalytic antibacterial effect of TiO2 film on TiAg on Streptococcus mutans," Angle Othodontist, vol. 79, pp. 528-532, 2009.
Dancer, S.J., "Importance of the environment in meticillin-resistant Staphylococcus aureus acquisition: the case for hospital cleaning," Lancet Infectious Diseases, vol. 8, pp. 101-113, 2008.
Chen et al., Science Xpress, pp. 1-10, online publication Jan. 20, 2011, Science. 1200448.
Inada, K., "Action spectra for photosynthesis in higher plants." Plant and Cell Physiology, vol. 17, pp. 355-365, 1976.
Mathews, et al., "Photocatalytic Effect of Light-Activated Nanoscale Formulations of TiO2 on Xanthomonas perforans and Control of Bacterial Spot of Tomato," Phytopathology vol. 103 pp. 228-236, 2013.
Teh et al., "Roles of titanium dioxide and ion-doped titanium eioxid on photocatalytic degradation of organic pollutants (phenolic compounds and dyes) in aqueous solutions: A review," Journal of Alloys and Compounds vol. 509 pp. 1648-1660, 2011.
Chen et al., "Investigation of transition metal ion doping behaviors on TiO2 nanoparticles," J. Nanoparticle Research vol. 10 pp. 163-171 (2008).
Yuan et al., "Influence of co-doping of Zn(II) + Fe(III) on the photocatalytic activity of TiO2 for phenol degradation," Materials Chemistry and Physics vol. 73, pp. 323-326 2002.
Pelaez et al., "A Review on the Visible Light Active Titanium Dioxide Photocatalysts for Environmental Applications," AppliedCatalysis B 125 (2012) 331-349.
GensNano Self-Sanitizing Green Coating brochure, GreeN Earth Nano Sicenec, Inc. May 2010.

\* cited by examiner

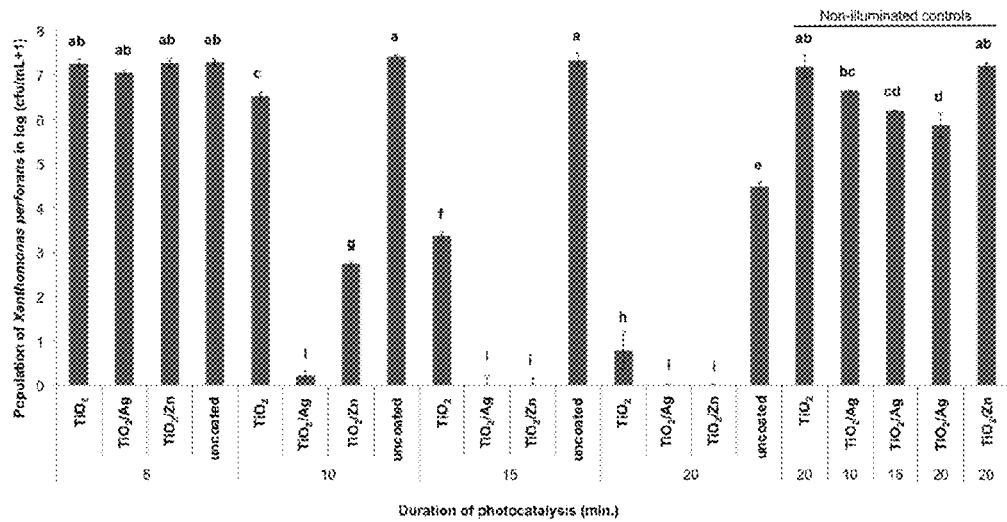
Figure 3. Photocatalytic killing of *Xanthomonas perforans*. Column means indicated with the same letters are not significantly different ($P \leq 0.05$) based on Student Newman Keuls test.
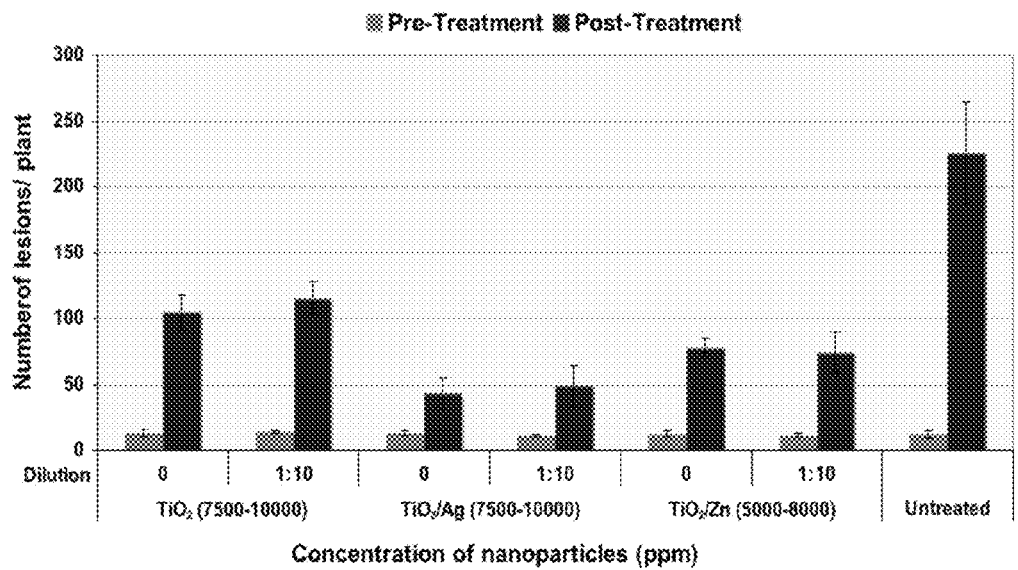
Figure 4:

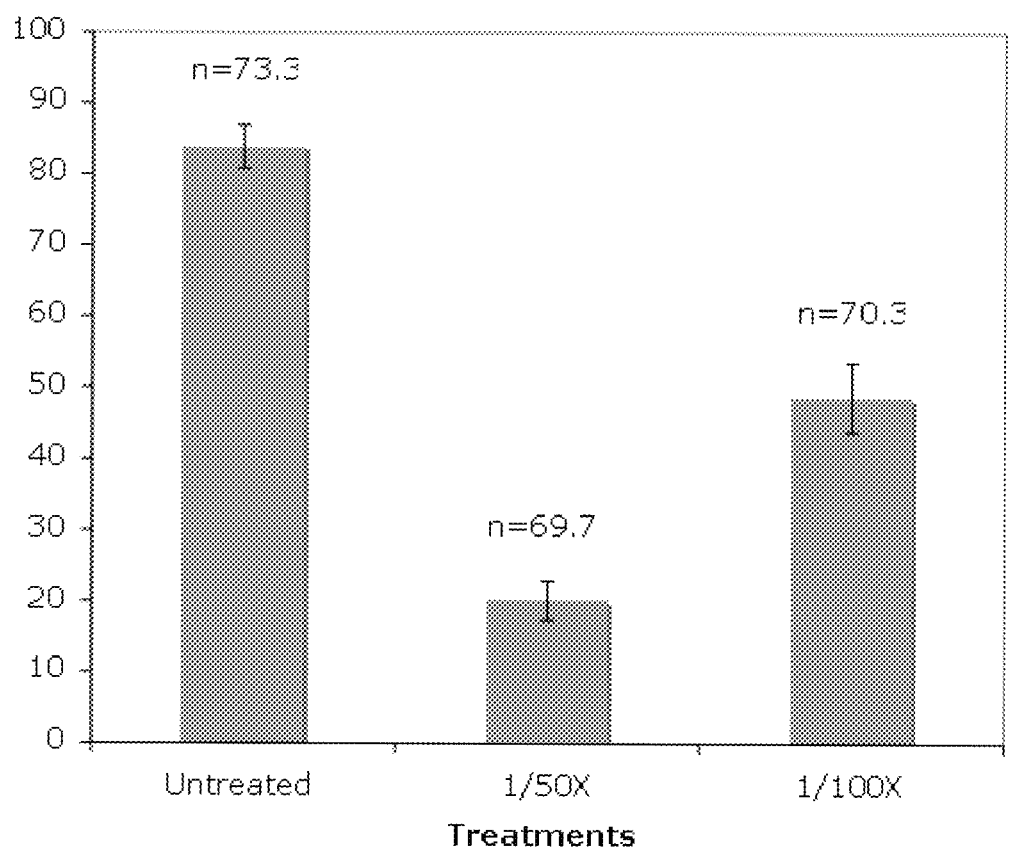
Figure 6: Percentage of lesions with conidia
* Error bar represents standard error of mean

TITANIUM DIOXIDE PHOTOCATALYTIC COMPOSITIONS AND USES THEREOF

CROSS-REFERENCE TO RELATED APPLICATIONS

This application is a continuation of U.S. application Ser. No. 14/713,020, filed May 15, 2015, which is a continuation of U.S. application Ser. No. 14/069,682, filed Nov. 1, 2013 (now U.S. Pat. No. 9,055,751), which is a divisional of U.S. application Ser. No. 13/463,495, filed May 3, 2012 (now U.S. Pat. No. 8,609,121), which claims the benefit of U.S. Provisional Application No. 61/482,393, filed May 4, 2011, each of which is incorporated herein by reference in its entirety.

FIELD

The present disclosure relates to novel photocatalytic compositions comprising titanium dioxide ($TiO_2$) nanoparticles, which are useful in the treatment of microbial diseases, more specifically, microbial diseases in plants.

BACKGROUND

In the past several decades, the development and exploration of the properties of materials led to the recognition of the photocatalytic nature of crystalline metal oxides such as $TiO_2$ (Fujishima et al., *Nature*, vol. 238, pgs. 37-38, 1972). Much effort has been devoted to research in this area resulting in a wide range of potential applications, such as sensors, photocatalysts, and photovoltaics. The properties of such materials depend on their chemical composition, size, and shape. In particular, as the particle size of the materials decreases, new physical and chemical properties may emerge as a result of the greatly increased surface area. However, the relationship between physical properties and the photocatalytic activities is complex, and optimal conditions and structures may vary from case to case, as discussed in Chen et al. extensive review of the methods of synthesis and the physicochemistry of $TiO_2$ nanoparticles (*Chemical Reviews*, vol. 107, pgs. 2891-2959, 2007).

Some years after the discovery of photocatalysis by $TiO_2$, studies showed that $TiO_2$ acts as a light-activated antimicrobial coating when irradiated for 60-120 minutes with ultraviolet (UV) radiation (387 nm); the coating was shown to have high bactericidal action against *Escherichia coli* and *Lactobacillus acidophilus* (Matsunaga et al., *FEMS Microbiology Letters*, vol. 29, pgs. 211-214, 1985). Subsequent work led to development of nanoscale $TiO_2$ formulations that can have inhibitory effects on a range of bacterial, fungal and viral organisms (for example, Tsuang et al., *Artificial Organs*, vol. 32, pgs. 167-174, 2008 and Choi et al., *Angle Orthodontist*, vol. 79, pgs. 528-532, 2009) including organisms that increase the risk of hospital acquired infection when present on surfaces (Dancer, S. J., *Lancet Infectious Diseases*, vol. 8, pgs. 101-113, 2008). Thus, when reduced microbial contamination on inanimate surfaces is desired, nanoscale $TiO_2$ coatings can be applied to that surface followed by UV illumination.

More recently, a few reports have emerged indicating that $TiO_2$ can be applied to plants to provide certain benefits. Kawai proposed that the photocatalyzed oxidative effect from application of a $TiO_2$ preparation degrades organic material and thereby increases local $CO_2$ concentrations at the leaf surface leading to increased plant sugar content, and also creates an antibacterial condition in at least some plants by the oxidation of plant lipids to induce endogenous plant defense mechanisms that reduce the impact of pathogenic microbes (U.S. Pat. No. 6,589,912). A commercial photocatalytic nanoscale $TiO_2$ with an average particle size of 30 nm was reported to accelerate blooming and fruiting and reduce the incidence of certain diseases (Japanese Patent No. 2006-632721). Another group also reported that $TiO_2$ particles averaging 30 nm reduced the extent of disease from two bacteria in cucumber leaves and also increased the photosynthetic rate (Zhang et al., *Nanoscience*, vol. 12(1), pgs. 1-6, 2007; Zhang et al., *Journal of Inorganic Materials*, vol. 23(1), pgs. 55-60, 2008; and Cui et al., *NSTI-Nanotech*, vol. 2, pgs. 286-289, 2009).

Nanoscale $TiO_2$ absorbs light in the UV range, but has very little absorbance in the visible range; this characteristic makes it a useful component in applications where protection from UV damage is helpful. However, in some applications it would be preferable to achieve the photocatalytic effect with longer wavelength light. For example, interior lighting generally exhibits minimal UV energy, greatly reducing the ability of nanoscale $TiO_2$ to exhibit photocatalysis. Similarly, greater photocatalytic efficiency in agricultural applications can reduce application rates and costs, and multiple benefits can be obtained by increasing the fraction of available solar irradiance captured by the photocatalyst. Thus, increasing the absorbance of longer wavelengths would allow the benefits of photocatalytic effects across a wider range of applications.

Investigation over many years has shown that the absorption spectrum of $TiO_2$ can be altered by introduction of doping agents that change the crystal lattice structure. A more recent report shows that the absorption spectrum can extend across the entire visible range to produce a material that is black to the human eye (Chen et al., *Science Xpress*, pgs. 1-10, online publication January 20, 2011, *Science*.1200448). However, such a broad absorbance spectrum is undesirable for use on plants, which are dependent on solar irradiation for photosynthesis.

The photosynthetic efficiency of plants varies across the electromagnetic spectrum. The number of photons of a given energy or wavelength that are needed to give a certain photosynthetic rate can be measured, and when this is determined across a range of wavelengths one obtains an action spectrum. Detailed action spectra have been reported over a wide range of monochromatic light for various plant species. A systematic study of the action spectra for 33 species of higher plants was reported (Inada, K., *Plant and Cell Physiology*, vol. 17, pgs. 355-365, 1976). Of interest is the observation that the action spectra for all herbaceous plants is generally similar, with a high and broad peak at 500-680 nm, which extends to a lower and narrower shoulder at about 435 nm, with a rapid decline at shorter wavelengths. The spectrum for arboreal plants is similar although the size of the 435 nm shoulder is reduced compared to herbaceous plants.

Thus, a need exists for an efficient photocatalytic material that absorbs electromagnetic energy efficiently for wavelengths below about 450 nm. Additional requirements for an optimized photocatalytic crop-protecting and yield-enhancing agent exist, including the cost and abundance of raw materials, ease of synthesis and application, and especially a low environmental toxicity and thus well established safety for any materials comprising the agent.

SUMMARY

The present disclosure relates to photocatalytic compositions comprising doped titanium dioxide ($TiO_2$) nanoparticles, which are useful in the treatment and prevention of microbial diseases and infestations, more specifically, microbial diseases and infestations in plants.

In one embodiment, the invention provides a photocatalytic composition comprising titanium dioxide ($TiO_2$) nanoparticles doped with zinc (Zn) and having a ratio of titanium dioxide to zinc from about 5 to about 150.

The photocatalytic composition can further comprise silicon dioxide ($SiO_2$). The ratio of titanium dioxide to silicon dioxide is from about 1 to about 500.

The titanium dioxide nanoparticles preferably have an average particle size of from about 2 nm to about 20 nm.

The photocatalytic compositions absorb electromagnetic radiation in a wavelength range from about 200 nm to about 500 nm, and the absorbance of light of wavelengths longer than about 450 nm is less than 50% the absorbance of light of wavelengths shorter than about 350 nm.

Further, the present invention provides for a method for preventing or treating microbial diseases and infestations in plants comprising applying the photocatalytic compositions taught herein to the surface of a plant. The present invention also provides for a method for crop-protecting and yield-enhancing of a plant comprising applying the photocatalytic compositions taught herein to the surface of the plant.

BRIEF DESCRIPTION OF THE DRAWINGS

FIG. 3 shows photocatalytic killing of *Xanthomonas perforans* on surfaces treated with various $TiO_2$ compositions using UV-A light.

FIG. 4 shows the effectiveness of various $TiO_2$ compositions in preventing/reducing the number of leaf spot lesions per plant in sunlight.

FIG. 5 shows the effectiveness of selected treatments for the control of olive knot in sunlight.

FIG. 6 shows the effect of various $TiO_2$ compositions on conidial development of *Sphaerotheca fuliginea/Erysiphe cichoracearum*, the fungal causal agent of powdery mildew, under sunlight.

DETAILED DESCRIPTION

The invention provides modified photocatalytic compositions that fulfill the requirement for a broadly useful photocatalytic product for use on plants, and demonstrate superiority over unmodified nanoscale $TiO_2$. Further, the appropriate application rates have been evaluated. The compositions prevent black leaf spot on tomato plants, increase the yield of marketable fruit, reduce powdery mildew conidia formation on cantaloupe, and protect olive plants from microbially-induced tumors. The compositions contain only well characterized and safe materials, and can be easily applied in the field using ordinary spray equipment. The improvements embodied in this invention afford the benefits of photocatalytic activity in settings of low UV irradiance, including interior artificial lighting.

The present invention relates to a photocatalytic composition comprising zinc (Zn) doped titanium dioxide ($TiO_2$) nanoparticles, which is useful in the treatment and prevention of microbial diseases and infestations, more specifically, microbial diseases in plants.

In one embodiment, the invention provides a photocatalytic composition comprising titanium dioxide ($TiO_2$) nanoparticles doped with zinc (Zn) having a ratio of titanium dioxide to zinc from about 5 to about 150. The ratio of titanium dioxide to zinc is preferably from about 40 to about 100.

The photocatalytic composition can further comprise silicon dioxide ($SiO_2$). The ratio of titanium dioxide to silicon dioxide is from about 1 to about 500, preferably from about 3 to about 20.

The titanium dioxide nanoparticles preferably have an average particle size of from about 2 nm to about 20 nm.

A particularly preferred embodiment of the present invention provides a photocatalytic composition which comprises:

(A) about 5000 to about 8000 ppm of titanium dioxide, (B) about 50 to about 100 ppm of zinc, and (C) about 500 to about 1000 ppm of silicon dioxide.

The photocatalytic composition absorbs electromagnetic radiation in a wavelength range from about 200 nm to about 500 nm, and the absorbance of light of wavelengths longer than about 450 nm is less than 50% the absorbance of light of wavelengths shorter than about 350 nm.

Another embodiment of the present invention provides for a method for treating or preventing microbial diseases and infestations in a plant comprising applying a photocatalytic composition comprising titanium dioxide ($TiO_2$) nanoparticles doped with zinc (Zn) having a ratio of titanium dioxide to zinc from about 5 to about 150, to the surface of a plant.

Examples of plants to be treated include, but are not limited to, crop plants, which includes herbaceous and woody crop plants, for example, tomato plants, cucumber plants, citrus plants, olive and other drupe plants, apple and other pome plants, nut plants, and ornamental plants.

Examples of microbial diseases include, but are not limited to, leaf spot disease, olive knot, fire blight, walnut blight, cherry canker, and powdery mildew.

The present invention also provides for a method for increasing crop yield of a plant comprising applying a photocatalytic composition comprising titanium dioxide ($TiO_2$) nanoparticles doped with zinc (Zn) having a ratio of titanium dioxide to zinc from about 5 to about 150, to the surface of a plant.

The present invention also provides for a method for treating or preventing microbial disease or infestation on a surface comprising applying a photocatalytic composition comprising titanium dioxide ($TiO_2$) nanoparticles doped with zinc (Zn) having a ratio of titanium dioxide to zinc from about 5 to about 150, to a surface illuminated by artificial light. The use herein of "surface" means an inanimate or an animate object including plants.

Further, the invention provides for a method for treating or preventing microbial diseases or infestations in a plant comprising applying a photocatalytic composition comprising titanium dioxide ($TiO_2$) nanoparticles doped with at least one doping agent, wherein the addition of the doping agent increases the absorbance of light across the range of about 200 nm to about 500 nm, and wherein the absorbance of light of wavelengths longer than about 450 nm is less than 50% the absorbance of light of wavelengths shorter than about 350 nm, to the surface of a plant. Preferably, the addition of the doping agent increases the absorbance of light across the range of about 350 nm to about 450 nm. The doping agent useful in the photocatalytic composition is selected from the group consisting of Ag, Zn, Si, C, N, S, Fe, Mo, Ru, Cu, Os, Re, Rh, Sn, Pt, Li, Na, and K, and combinations thereof. Particularly preferred doping agents are Zn, Si, and Ag.

Figure 1:
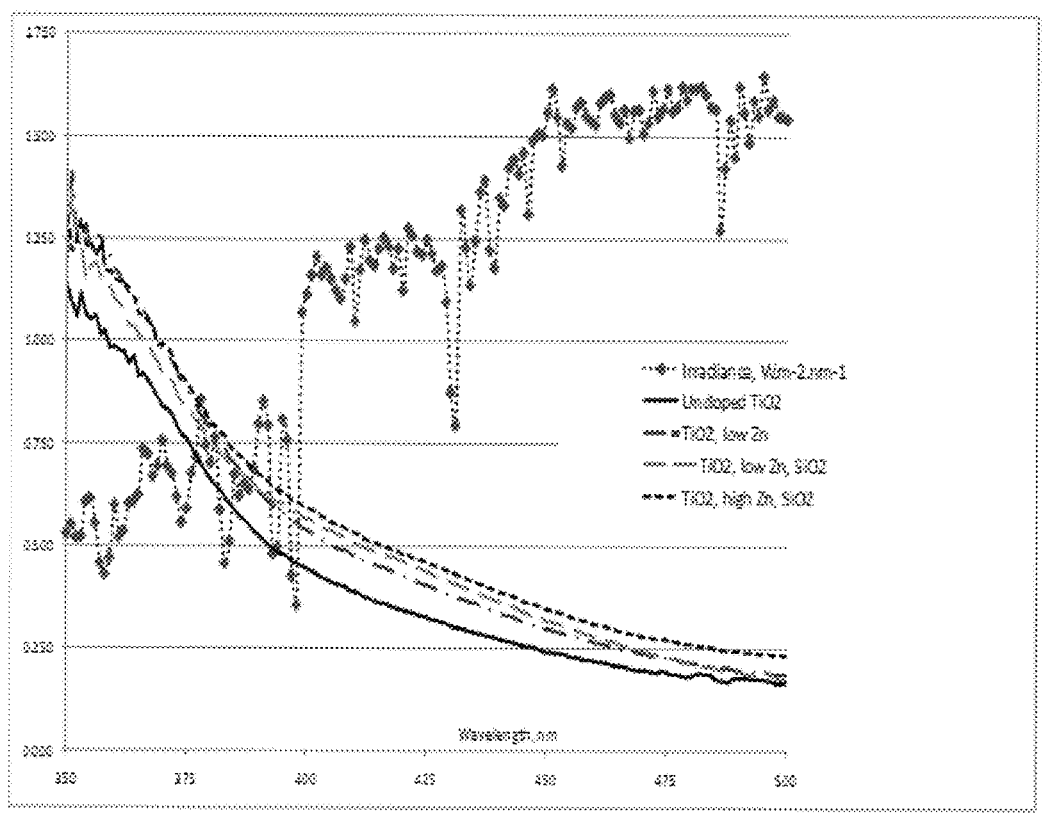
FIG. 1 is a graphic representation of solar energy capture of various $TiO_2$ compositions.

Further, the invention provides for a photocatalytic composition which absorbs electromagnetic radiation in a wavelength range from about 200 nm to about 500 nm, and the absorbance of light of wavelengths longer than about 450 nm is less than 50% the absorbance of light of wavelengths shorter than about 350 nm. The composition comprises titanium dioxide nanoparticles doped by at least one doping agent, wherein the doping agent disrupts the crystal lattice structure of the titanium dioxide nanoparticles thereby altering the absorbance spectrum of the composition.

The invention provides photocatalytic materials that absorb an increased proportion of available electromagnetic energy in a wavelength range that is selected to not substantially interfere with photosynthesis. However, it will be appreciated that the utility of the present invention is not limited to agricultural uses, since improved utilization of the energy of light of wavelengths below 500 nm can afford benefit in a variety of settings. The invention is not limited to any particular theory or mechanism of photocatalytic benefit, since photocatalysis may provide benefit by multiple mechanisms, and we do not limit the invention to a particular composition or type of photocatalyst. Also, the synthetic methods used to manufacture such materials may be varied, and we do not limit the invention as to a particular mode of manufacture.

Further, while the examples given here are based on $TiO_2$, a variety of other photocatalysts such as $Fe_2O_3$ also may be similarly optimized, for example by inclusion of $SnO_2$ at differing levels, and are contemplated in this invention. The present invention is illustrated by the use of formulations of the invention dispersed in water for convenient application to a wide range of surfaces, but preparations contemplated in the invention also may be dispersed in other solvents, and also may utilize colorants, dispersants, carriers, and amphipathic agents to facilitate ease of use or uniform application in selected settings.

Other than in the operating examples, or where otherwise indicated, all numbers expressing quantities of ingredients are to be understood as being modified in all instances by the term "about".

"At least one" as used herein means one or more and thus includes individual components as well as mixtures/combinations.

The term "comprising" (and its grammatical variations) as used herein is used in the inclusive sense of "having" or "including" and not in the exclusive sense of "consisting only of."

The terms "a" and "the" as used herein are understood to encompass the plural as well as the singular.

The terms "doped" or "doping" as used herein are understood to encompass the introduction of one or more impurities (e.g., dopant, doping agent) into a material for the purpose of modifying the properties of the material.

The terms "treatment" and "treating" include mitigation of a pre-existing microbial disease or infestation.

The terms "prevention" and "prophylaxis" include reduction of the incidence or severity of disease or infestation in either individuals or populations.

The invention will be further understood by the following examples, which are intended to be illustrative of the invention, but not limiting thereof.

EXAMPLES

Example 1

Absorption characteristics of nanoscale $TiO_2$ were compared to nanoscale $TiO_2$ doped with two differing zinc levels and $SiO_2$, over the wavelength range of 350 nm to 500 nm. The nanoparticle compositions were manufactured by a modified sol-gel process, to produce formulations containing nanoparticles of anatase $TiO_2$ whose average size was 6 to 7 nm. Zinc was incorporated as a doping agent to provide either low zinc content (0.125% relative to $TiO_2$) or high zinc content (1.25% relative to $TiO_2$). When $SiO_2$ was an additional dopant, it was present at 10% relative to $TiO_2$. The preparations were dried and absorbance was measured using standard methods for obtaining diffuse reflectance spectra (DRS) of powders. The solar irradiance (hemispherical, 37 degree tilt) from ASTM G173-03 across this spectral range is shown for reference. (See FIG. 1).

It is evident upon inspection that the $TiO_2$ preparations doped with hetero-atoms absorb more strongly than otherwise similar undoped $TiO_2$ in the near-UV and violet region of the spectrum. The doped preparations absorb 25 to 35 percent more of the energy available from 400 to 450 rim, a region where solar irradiance is relatively high but still outside the main photosynthetic action spectrum of plants.

Example 2

Photocatalytic Activity of Various Formulations of $TiO_2$ Doped with Zn and $SiO_2$ under UV Illumination The four formulations described in Example 1 were tested for their photocatalytic activity in a standardized system. Each preparation was suspended in water at approximately 8000 ppm and applied to a glass panel using a robotic high volume low pressure sprayer, and allowed to dry for 24 hours. These panels were each attached to a glass tube to form a container, into which was placed 30 ml of an aqueous solution of methylene blue at a concentration providing an optical density of 2.3 at 664 nm. The tubes were covered with a glass panel and subjected to illumination at an energy density of approximately 0.5 $mW/cm^2$ from a lamp (GE item F18T8/BLB) affording ultraviolet illumination at 354 nm. This lamp provides no light at wavelengths below 300nm or above 400 nm. The optical density of the methylene blue solution in each sample was monitored over a period of 48 hours and is shown in FIG. 2.

Figure 2:
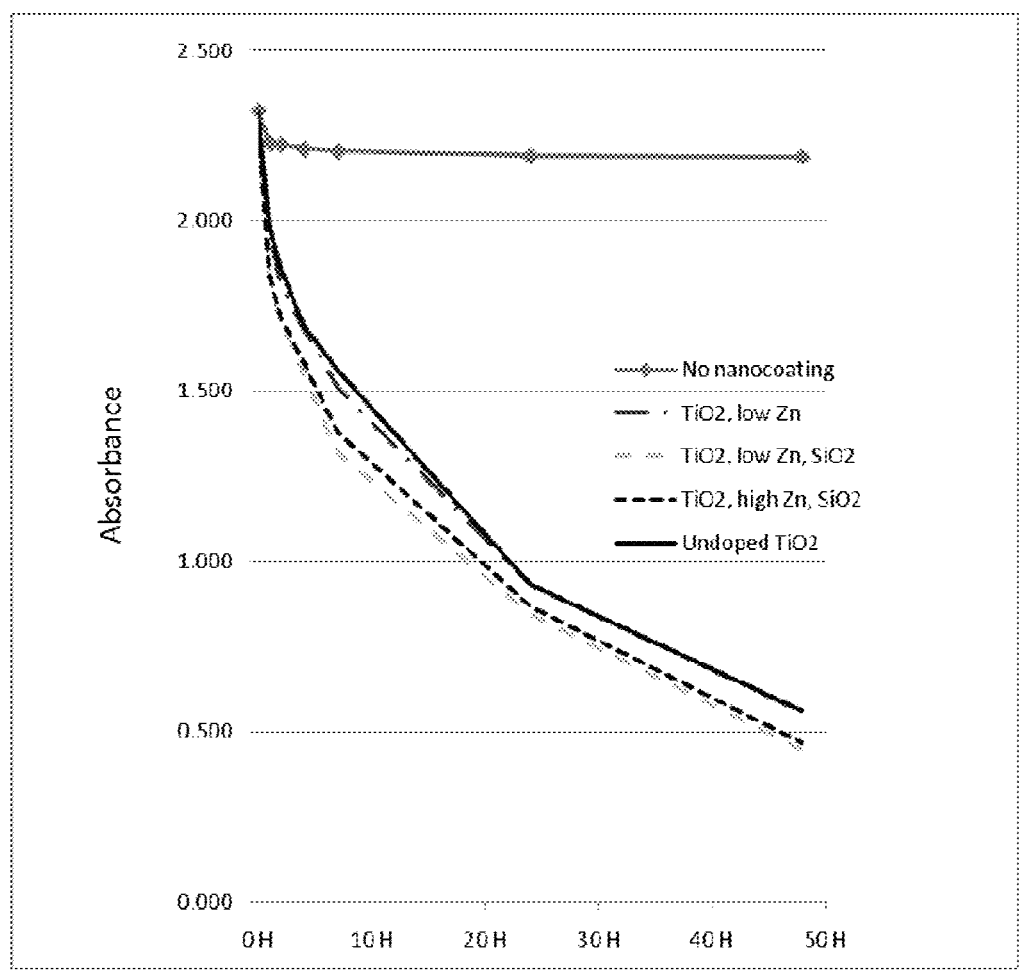
FIG. 2 is a graphic representation of the photocatalytic activity of various $TiO_2$ compositions when irradiated at 354 nm.

FIG. 2 shows that the nanocoatings caused a decline in optical density, which results from photocatalytic degradation of the organic dye methylene blue. The coatings that had the higher amounts of dopants afforded the most rapid declines, consistent with greater absorbance of light from the lamp in the UV range (354 nm).

Example 3

Photocatalytic Activity of Various Formulations of $TiO_2$ Doped with Zn and $SiO_2$ under Visible Light Illumination The four formulations described in Example 1 were tested for their photocatalytic activity in a second system, in which the experimental illumination was changed to more closely mimic relevant illumination such as daylight or interior light, which are deficient in the ultraviolet energy used in Example 2. Also, for this example the nanoparticle formulations were evaluated as colloidal suspensions in 20 mM phosphate buffer, pH 7.2, rather than on a static surface. The experiment was performed in a 96-well plate format, in which each well contained methylene blue (observed $OD_{655}$ ranging from 0.05 to 0.5) and a nanoparticle formulation or appropriate controls in a final volume of 200 microliters. The plate was illuminated from a distance of 20 cm with light from two Sylvania Gro-Lux lamps (F20 T12 GRO/AQ). These lamps emit only 2% of their total emitted energy below 400 nm, whereas approximately 36% of their total energy is emitted between 380 and 500 nm, with a peak at 436 nm (reference: Technical Information Bulletin "Spectral Power Distributions of Sylvania Fluorescent Lamps", Osram Sylvania, www.sylvania.com).

The compositions of the four preparations tested in this experiment were independently verified by the analytical technique known as ICP-AES (inductively coupled plasma atomic emission spectrometry), which demonstrated their equivalent $TiO_2$ content and variations in Si and Zn composition as described in Example 1. The nanoparticle preparations were diluted in buffer to provide final concentrations of 75 ppm of titanium dioxide of each formulation, with twenty replicate wells of each formulation. After a short period of equilibration in the dark, each plate was exposed to illumination with shaking, and optical density at 655 nm was measured at multiple times over using a Molecular Devices SpectraMax Plus spectrophotometer. The observed linear declines in optical density due to each formulation were measured to give the rates summarized in Table 1:

TABLE 1

|  | Trial 1 | Trial 2 |
| --- | --- | --- |
| $TiO_2$, low Zn | 0.0017* | 0.0016 |
| $TiO_2$, low Zn, high Si | 0.0020 | Not tested |
| $TiO_2$, high Zn, high Si | 0.0019 | Not tested |
| $TiO_2$ only | Not tested | 0.0013 |

*All values reported are the decline in optical density at 655 nm, per minute

It is evident that all the doped $TiO_2$ formulations show significantly increased rates (25% to 50%) compared to the undoped $TiO_2$ formulation. The magnitude of the increase in the rate of photocatalytic activity is highly consistent with the increased absorption of light energy in the range of 400 nm to 450 nm that is evident in the spectra described in Example 1.

Example 4

Photocatalytic Killing of the Plant Pathogen *Xanthomonas Perforans* on a Surface Using Incandescent Light Sterile glass cover slips were separately coated with 0.5 ml volumes of one of several types of nanoparticle suspensions ($TiO_2$, $TiO_2$/Ag or $TiO_2$/Zn). The nanoparticle compositions, comparable to those in Example 2, were manufactured by a modified sol-gel process, to produce formulations containing nanoparticles of anatase $TiO_2$ whose average size was 6 to 7 nm, and which were doped with either Ag or Zn, using a ratio of $TiO_2$ to dopant of approximately 400:1 and approximately 800:1 respectively. The coverslips were dried under sterile conditions. A standardized inoculum of 0.1 ml of water containing $10^7$ copper-resistant *Xanthomonas Perforans* was applied to treated and untreated coverslips. The coverslips were then either illuminated with incandescent light at an illumination density of $3 \times 10^4$ lux or maintained in a dark environment. At intervals, coverslips were placed in sterile centrifuge tubes containing 10 ml of sterile water and vortexed. The recovered bacteria were collected by centrifugation (14000×g, 3 minutes) and suspended in 1 ml of sterile water. The numbers of viable bacteria in the resulting suspensions were enumerated by standard plate dilution methods. The results are shown in FIG. 3.

Examination of FIG. 3 shows that the nanoparticle treatments resulted in a time-dependent and light-dependent killing of bacteria that is not observed on the untreated coverslips. The rate of killing was faster for the doped preparations than for undoped $TiO_2$. Of interest is the absence of bacterial killing by non-illuminated $TiO_2$/Zn and $TiO_2$, whereas the $TiO_2$/Ag showed some killing of bacteria even when not illuminated, illustrating both the greater native toxicity of the material containing Ag, and the requirement for illumination to provide energy for the photocatalytic anti-bacterial effect.

Example 5

Infection of Tomato Plants by *Xanthomonas Perforans*, a Causative Agent of Leaf Spot, is Reduced by Treatment with Photocatalytic Materials Many bacterial diseases of plants are caused by uncontrolled expansions of pre-existing populations of bacteria, which in low numbers do not cause disease. Thus, a major method to control these diseases in agriculture is to reduce the population of viable bacteria in order to preclude excessive expansion of bacteria that lead to damage and disease of the plant. Bacterial leaf spot of tomato is a disease system where such a preventative approach is commonly sought.

A seed lot of tomato cultivar BHN 602 was naturally infected with *Xanthomonas perforans* strain Xp1-7. The infected plants were treated at the 3-4 leaf stage with nanoparticles ($TiO_2$, $TiO_2$/Ag & $TiO_2$/Zn) either undiluted or after tenfold dilution. The nanoparticle compositions, comparable to those in Example 4, were manufactured by a modified sol-gel process, to produce formulations containing nanoparticles of anatase $TiO_2$ whose average size was 6 to 7 nm, and which were doped with either Ag or Zn, using a ratio of $TiO_2$ to dopant of approximately 400:1 and approximately 800:1 respectively. The nanoparticles were suspended in water at concentration of 7,500-10,000 ppm or 5,000 to 8,000 ppm as indicated in FIG. 4. The plants were irrigated daily to keep the soil moisture level at 85-95% and misted with water two times a day for 15 minutes each to enhance pathogen growth. Three plants were tested for each treatment and the trial was set-up in a randomized complete block design. Bacterial spot lesions were recorded before and two weeks after the treatment. Results are shown in FIG. 4. The error bar represents the standard error of the mean.

It is evident that all nanoparticle treatments reduced the number of bacterial spot lesions. The effectiveness of each preparation was not significantly affected by a ten-fold dilution in this experiment. Notably, the addition of a doping agent to the $TiO_2$ nanoparticles improved effectiveness compared to undoped $TiO_2$, consistent with increased photocatalytic activity.

Example 6

Protection from Olive Knot Caused by *Pseudomonas Syringae* pv. *Savastonoi*

Olive knot is a disease of olive trees caused by *P. syringae* pv *savastonoi*, a motile gram negative bacterium that creates tumors (knots) in olive trees. The organism survives in these knots and is dispersed during wet periods, whereupon it enters new sites via wounds including leaf and flower abscission scars and those induced by mechanical injury from wind, pruning, or frost. These knots inhibit proper plant growth and reduce fruit production. As in many other bacterial diseases of plants, a reduction in the population of bacteria before disease is evident prevents or reduces the occurrence of olive knot, and methods to reduce the bacterial population are thus a common approach in agriculture.

In a greenhouse study, leaf scar wounds were inoculated with either $10^5$ or $10^8$ P. syringae bacteria, and then sprayed a with a fifty-fold dilution of the $TiO_2$/low Zn preparation described in Example 1, thus providing a 250 ppm aqueous suspension, using a hand sprayer. Several other agents were tested as controls. These control agents include Vantocil B (a combination of poly(hexamethylenebiguanideHCl with alkyldimethyl ammonium chloride), from Arch Chemicals, Inc, now part of Lonza Goup Ltd, Basel Switzerland); Deccosan 321 (a mixture of several quaternary ammonium salts, from Decco Cerrexagri Inc, Monrovia CA USA); Kasumin (kasugamycinHCl, from Arysta Lifescience N. A. LLC, Cary N.C. USA); Citrox (a proprietary mixture of citrus oil, detergent, and hydrogen peroxide, manufactured by Misco Products Corporation, Reading Pa., USA); and Kocide 3000 (copper hydroxide, from DuPont Crop Protection, USA). The inoculated sites were wrapped with a single layer of Parafilm for one day to maintain enough moisture to ensure high rates of infection, even though this reduced the amount of light at the inoculation site.

Figure 5:
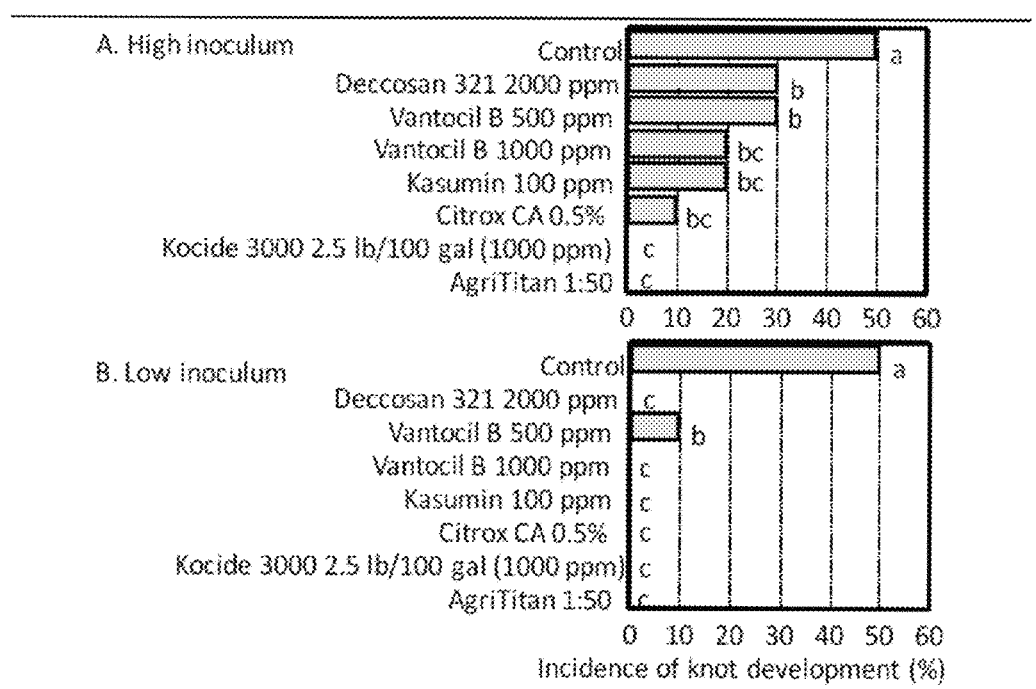

The first evidence for knot formation was observed after one month, and a quantitative first evaluation was performed after seven weeks. At the lower challenge inoculum, the nanoparticle $TiO_2$/low Zn treatment (termed AgriTitan in FIG. 5) was completely effective, similar to most other tested agents (FIG. 5). At the higher challenge inoculum, the spray treatment with 250 ppm $TiO_2$/low Zn continued to be fully effective, similar to the current standard treatment of 1000 ppm copper hydroxide. All other tested agents were less effective (FIG. 5).

Example 7

Tomato Field Experiment

The $TiO_2$ preparation doped with Zn used in the greenhouse experiment was selected for use in a field trial. Zn was selected as the dopant for further investigation due to its approval by the U.S. Environmental Protection Agency as a minimal risk pesticide, a status not accorded other potential doping agents. Field trials were performed to compare the effectiveness of $TiO_2$ doped with Zinc at a ratio of 800:1 (formulated as a 0.7% colloidal suspension in $H_2O$) to standard treatments for prevention or control of leaf spot on tomato plants. Each treatment group contained 48 plants (12 per plot, 4 replicates), and the trial used a randomized complete block design. The $TiO_2$/Zn was diluted in water to provide a range of application rates. Controls included a copper sulfate formulation either alone or in conjunction with manzate, and no treatment.

The plants were sprayed with test materials at weekly intervals (8 times) starting from the first week after transplanting. Disease severity was rated at monthly intervals using a non-dimensional 12-point scale, to assess the percentage of canopy affected by bacterial leaf spot (Horsfall et al., Phytopathology, vol. 35, 655, Abstract, 1945). These values were converted to mid-percentages and used to generate an Area Under Disease Progression Curve (AUDPC). Marketable yield data based on USDA grades also were taken from the field trial to determine whether the nanoscale formulations had any herbicidal action on tomato plants. The results are shown in Table 2 and Table 3.

TABLE 2

Effect of $TiO_2$/Zn on the incidence of bacterial spot on tomato (variety BHN 602), shown as average area under the disease progress curve (AUDPC).

| Treatment | Dilution | AUDPC[y] |
|---|---|---|
| $TiO_2$/Zn | X/10[x] | 800.6 c[z] |
| | X/20 | 950.3 bc |
| | X/40 | 1000.1 b |
| | X/60 | 1033.4 ab |
| | X/80 | 933.6 bc |
| | X/100 | 1050.0 ab |
| Copper | | 1050.0 ab |
| Copper + Manzate | | 1033.4 ab |
| Untreated | | 1181.3 a |

[x] X represents the undiluted formulation of $TiO_2$/Zn.
[y] Disease severities were rated using the Horsfall-Barratt scale, a non-dimensional 12-point scale, to assess the percentage of canopy affected by bacterial spot. Values were converted to mid-percentages and used to generate AUDPC.
[z] Column means indicated with the same letters are not significantly different ($P \leq 0.05$) based on Student Newman Keuls test.

The results of the field trial summarized in Table 2 show that $TiO_2$/Zn provided better protection against spontaneous leaf spot disease than either of the conventional treatments. In pair-wise comparisons, the 1:10 diluted $TiO_2$/Zn was statistically significantly better than either of the control treatments, demonstrating more than a 20% reduction in the AUDPC. Also, a comparison of the results for all dilutions of $TiO_2$/Zn as a group to the controls as a group showed statistical significance (p<0.05).

TABLE 3

Effect of $TiO_2$/Zn on the yield of tomato (kg/ha).

| | | Yield (kg/ha)[y] | | | |
|---|---|---|---|---|---|
| Treatment | Dilution | Medium | Large | Extra Large | Total Marketable |
| $TiO_2$/Zn | X/10[x] | 10047 a[z] | 18581 a | 38563 a | 67191 a |
| | X/20 | 8702 a | 16070 ab | 38622 a | 63394 a |
| | X/40 | 9248 a | 18779 a | 32594 a | 60620 a |
| | X/60 | 8397 a | 16980 ab | 40102 a | 65478 a |
| | X/80 | 6393 a | 16392 ab | 32446 a | 55231 a |
| | X/100 | 8457 a | 18319 a | 35091 a | 61867 a |
| Copper | | 7744 a | 13642 b | 32006 a | 53392 a |
| Copper + Manzate | | 7653 a | 14549 b | 35656 a | 57859 a |
| Untreated | | 6312 a | 15293 ab | 32670 a | 54364 a |

[x] X represents the undiluted formulation of $TiO_2$/Zn.
[z] Column means indicated with the same letters are not significantly different ($P \leq 0.05$) based on Student Newman Keuls test.

The results of the field trial summarized in Table 3 show that $TiO_2$/Zn did not adversely affect the yield of marketable tomato. In fact, increased yields were observed for the $TiO_2$/Zn treated groups; the total marketable yield from the plants treated with the tenfold diluted $TiO_2$/Zn material was more than 20% greater than the yield from any control. Although this difference was not statistically significant in individual pair-wise comparisons owing to variations in yield within in each group, a statistical test comparing the "total marketable" results for the six dilutions of $TiO_2$/Zn as a group to the three control treatments as a group was statistically significant (p<0.05).

Example 8

A replicate of Example 7 was performed in the next growing season. The protocol was identical to Example 7, wherein various dilutions of the nanoscale $TiO_2$ /low Zn aqueous preparation were applied weekly by conventional high volume, low pressure compressed air spray to tomatoes in the field in a random block design, with appropriate controls. The results for disease progression are presented in Table 4, below, and demonstrate a concentration dependent control of disease. Unfortunately, yield data are not available for this experiment due to severe damage from a hailstorm prior to fruit harvest.

TABLE 4

Effect of $TiO_2$/Zn on the incidence of bacterial spot on tomato cultivar 'BHN 602', shown as average area under the disease progress curve (AUDPC).

| Treatment | Dilution$^x$ | AUDPC$^y$ |
|---|---|---|
| $TiO_2$/Zn | X/10 | 583.6 d$^z$ |
|  | X/20 | 741.1 abc |
|  | X/40 | 724.5 bc |
|  | X/60 | 752.5 abc |
|  | X/80 | 757.8 abc |
|  | X/100 | 806.8 ab |
| Kocide 3000 |  | 864.5 ab |
| Kocide3000 + Penncozeb 75DF |  | 642.3 cd |
| Untreated |  | 892.9 a |
| LSD |  | 107.50 |
| P > F |  | <0.0001 |

$^x$X represents the undiluted formulation of $TiO_2$/Zn.
$^y$Disease severities were rated using the Horsfall-Barratt scale, a non-dimensional 12-point scale, to assess the percentage of canopy affected by bacterial spot. Values were converted to mid-percentages and used to generate AUDPC.
$^z$Column means indicated with the same letters are not significantly different (P ≤ 0.05) based on Student Newman Keuls test.
Yield data could not be taken due to significant hail damage on tomatoes one week before the first harvest date.

Example 9

A third field trial in the tomato spot disease system was conducted in the next growing season. Based on the results of Example 7 and Example 8, we did not test the more dilute application rates of $TiO_2$/Zn, and thus the ability to detect a clear relationship to the applied rates was reduced. However, the general result remained the same (Table 5).

TABLE 5

Effect of $TiO_2$/Zn on the incidence of bacterial spot on tomato cultivar 'BHN 602', shown as average area under the disease progress curve (AUDPC), and the yield of tomato fruit.

| | | Yield (kg/ha) | | | | |
|---|---|---|---|---|---|---|
| Treatment | Dilution$^x$ | Medium | Large | Extra Large | Total Marketable | AUDPC$^y$ |
| $TiO_2$/Zn | X/10 | 4,518 a$^z$ | 7,512 a | 15,251 a | 27,281 a | 995.8 c |
|  | X/20 | 4,966 a | 6,994 a | 11,200 a | 23,161 a | 1,073.6 bc |
|  | X/40 | 4,210 a | 7,900 a | 17,409 a | 29,519 a | 1,089.4 bc |
| Kocide 3000 |  | 4,532 a | 6,986 a | 11,258 a | 22,776 a | 1,306.4 ab |
| Kocide 3000 + Penncozeb 75 DF |  | 3,909 a | 8,202 a | 14,933 a | 27,044 a | 816.4 c |
| Untreated |  | 5,449 a | 7,093 | 15,159 a | 27,700 a | 1,410.5 a |
| LSD |  | ns | ns | ns | ns | 277.3 |
| P > F |  | 0.7194 | 0.9652 | 0.4146 | 0.7845 | 0.0037 |

$^x$X represents the undiluted formulation of $TiO_2$/Zn.
$^y$Disease severities were rated using the Horsfall-Barratt scale, a non-dimensional 12-point scale, to assess the percentage of canopy affected by bacterial spot. Values were converted to mid-percentages and used to generate AUDPC.
$^z$Column means indicated with the same letters are not significantly different (P ≤ 0.05) based on Student Newman Keuls test.

Thus, in this third field trial, the application of nanoparticles of $TiO_2$ /low Zn again demonstrated activity in controlling bacterial spot of tomato, on the basis of disease severity and fruit yield. At a dilution of 1:10, $TiO_2$/Zn was statistically superior to either single agent copper or untreated controls.

Example 10

The Effect of $TiO_2$/Zn, Formulated as in Examples 7 and 8, on Conidial Development of *Sphaerotheca Fuliginea/Erysiphe Cichoracearum*, the Fungal Causal Agent of Powdery Mildew Cucumber plants with an approximately equal number of lesions on the leaves were tagged for the experiment in greenhouse conditions. Three leaves were used for each treatment. In FIG. 6, "n" represents the average number of lesions on these leaves. The lesions were in the range (0.1-0.6 cm). The plants were sprayed with $TiO_2$/Zn of formula 1 at 1/50 and 1/100× concentrations using a hand sprayer. Untreated plants were sprayed with sterile distilled water. The plants were kept in the greenhouse for 48 hours. Leaves were removed from the plants and lesions were observed under a microscope for presence or absence of conidia. (See FIG. 6).

These results show that application of the photocatalytic preparation significantly reduced the ability of powdery mildew to produce conidia, which are essential to its reproduction.

It is important to note that the construction and arrangement of the methods and steps shown in the exemplary embodiments is illustrative only. Although only a few embodiments of the present disclosure have been described in detail, those skilled in the art will readily appreciate that many modifications are possible without materially departing from the novel teachings and advantages of the subject matter recited in the claims. Accordingly, all such modifications are intended to be included within the scope of the present disclosure as defined in the appended claims. The order or sequence of any process or method steps may be varied or re-sequenced according to alternative embodiments. Other substitution, modification, changes and omissions may be made in the design, operating conditions and arrangement of the embodiments without departing from the spirit of the present disclosure as expressed in the appended claims.

All publications, patents and patent applications cited in this specification are herein incorporated by reference, and for any and all purposes, as if each individual publication, patent or patent application were specifically and individually indicated to be incorporated by reference. In this case of inconsistencies, the present disclosure will prevail.

The invention claimed is:

1. An inanimate object coated with a photocatalytic composition, wherein the photocatalytic composition comprises titanium dioxide ($TiO_2$) nanoparticles dispersed in water on a surface and wherein each singular $TiO_2$ nanoparticle is doped with zinc and at least one other doping agent.

2. The inanimate object according to claim 1, wherein the other doping agent is selected from the group consisting of Ag, Si, C, N, S, Fe, Mo, Ru, Cu, Os, Re, Rh, Sn, Pt, Li, Na and K, and combinations thereof.

3. The inanimate object according to claim 1, wherein the other doping agent is selected from the group consisting of Si and Ag.

4. The inanimate object according to claim 1, wherein the other doping agent is silicon dioxide.

5. The inanimate object according to claim 1, wherein the photocatalytic composition has a ratio of titanium dioxide to zinc of from about 5 to about 150.

6. The inanimate object according to claim 1, wherein the photocatalytic composition has a ratio of titanium dioxide to zinc of from about 40 to about 100.

7. The inanimate object according to claim 1, wherein the $TiO_2$ nanoparticles have an average particle size of from about 2 nm to about 20 nm.

8. The inanimate object according to claim 4, wherein the photocatalytic composition comprises:
   (A) about 5000 ppm to about 8000 ppm of titanium dioxide;
   (B) about 50 ppm to about 100 ppm of zinc; and
   (C) about 500 ppm to about 1000 ppm of silicon dioxide.

9. The inanimate object according to claim 1, wherein the photocatalytic composition absorbs electromagnetic radiation in a wavelength range from about 200 nm to about 500 nm, and the absorbance of light of wavelengths longer than about 450 nm is less than 50% the absorbance of light of wavelengths shorter than about 350 nm.

10. The inanimate object according to claim 1, wherein the zinc and the at least one other doping agent increases the absorbance of light across the range of about 350 nm to about 450 nm.

11. An inanimate object coated with a photocatalytic composition, wherein the photocatalytic composition consists essentially of titanium dioxide ($TiO_2$) nanoparticles doped with zinc and at least one other doping agent.

12. The inanimate object according to claim 11, wherein the other doping agent is selected from the group consisting of Ag, Si, C, N, S, Fe, Mo, Ru, Cu, Os, Re, Rh, Sn, Pt, Li, Na and K, and combinations thereof.

13. The inanimate object according to claim 11, wherein the other doping agent is selected from the group consisting of Si and Ag.

14. The inanimate object according to claim 11, wherein the other doping agent is silicon dioxide.

15. The inanimate object according to claim 11, wherein the photocatalytic composition has a ratio of titanium dioxide to zinc of from about 5 to about 150.

16. The inanimate object according to claim 11, wherein the photocatalytic composition has a ratio of titanium dioxide to zinc of from about 40 to about 100.

17. The inanimate object according to claim 11, wherein the $TiO_2$ nanoparticles have an average particle size of from about 2 nm to about 20 nm.

18. The inanimate object according to claim 14, wherein the photocatalytic composition consists essentially of:
   (A) about 5000 ppm to about 8000 ppm of titanium dioxide;
   (B) about 50 ppm to about 100 ppm of zinc; and
   (C) about 500 ppm to about 1000 ppm of silicon dioxide.

19. The inanimate object according to claim 11, wherein the photocatalytic composition absorbs electromagnetic radiation in a wavelength range from about 200 nm to about 500 nm, and the absorbance of light of wavelengths longer than about 450 nm is less than 50% the absorbance of light of wavelengths shorter than about 350 nm.

20. The inanimate object according to claim 11, wherein the zinc and the at least one other doping agent increases the absorbance of light across the range of about 350 nm to about 450 nm.

* * * * *